(12) United States Patent
Bothorel et al.

(10) Patent No.: US 8,979,364 B2
(45) Date of Patent: Mar. 17, 2015

(54) COMBINED PANORAMIC AND COMPUTED TOMOGRAPHY APPARATUS

(75) Inventors: Sylvie Bothorel, Paris (FR); Philippe Maillet, Marne la Vallee (FR); Jean-Marc Inglese, Bussy Saint Georges (FR)

(73) Assignee: Trophy, Mame la Vallee, Cedex (FR)

( * ) Notice: Subject to any disclaimer, the term of this patent is extended or adjusted under 35 U.S.C. 154(b) by 693 days.

(21) Appl. No.: 13/265,361

(22) PCT Filed: May 3, 2010

(86) PCT No.: PCT/IB2010/001298
§ 371 (c)(1),
(2), (4) Date: Oct. 20, 2011

(87) PCT Pub. No.: WO2010/128404
PCT Pub. Date: Nov. 11, 2010

(65) Prior Publication Data
US 2012/0039436 A1    Feb. 16, 2012

Related U.S. Application Data

(60) Provisional application No. 61/175,095, filed on May 4, 2009.

(51) Int. Cl.
*A61B 6/14*    (2006.01)
*A61B 6/00*    (2006.01)

(52) U.S. Cl.
CPC .................. *A61B 6/14* (2013.01); *A61B 6/4435* (2013.01)
USPC ............................................. 378/191; 378/38

(58) Field of Classification Search
CPC ........ A61B 6/035; A61B 6/14; A61B 6/4266; A61B 6/4417; A61B 6/4429; A61B 6/4435; A61B 6/4441
USPC .......................................... 378/4, 38–40, 191
See application file for complete search history.

(56) References Cited

U.S. PATENT DOCUMENTS

| 5,677,940 A | 10/1997 | Suzuki et al. |
| 6,118,842 A | 9/2000 | Arai et al. |

(Continued)

FOREIGN PATENT DOCUMENTS

| CN | 1787779 | 6/2006 |
| EP | 1 609 419 A1 | 12/2005 |

(Continued)

OTHER PUBLICATIONS

International Search Report mailed on Sep. 7, 2009 for International Application No. PCT/FR2008/001680, 3 pages.

(Continued)

*Primary Examiner* — Thomas R Artman

(57) ABSTRACT

A combined imaging apparatus for x-ray imaging of a subject in multiple modes has a supporting structure having an extended rotary arm, wherein the rotary arm has a computed tomography detector and a panoramic imaging detector, both mounted adjacently against a movable platen. A detector positioning apparatus is actuable to translate the position of the movable platen to either of at least first and second positions with respect to an x-ray source. The first position disposes the computed tomography detector in the direct path of an x-ray source and the second position disposes the panoramic imaging detector in the direct path of the x-ray source.

17 Claims, 14 Drawing Sheets

(56) References Cited

U.S. PATENT DOCUMENTS

| | | | |
|---|---|---|---|
| 6,289,074 B1 | 9/2001 | Arai et al. | |
| 6,334,708 B1* | 1/2002 | Kosugi | 378/197 |
| 6,619,839 B2 | 9/2003 | Yoshimura | |
| 7,236,563 B2 | 6/2007 | Sa et al. | |
| 7,315,608 B2* | 1/2008 | Sa et al. | 378/38 |
| 7,424,091 B2* | 9/2008 | Park et al. | 378/39 |
| 7,486,759 B2 | 2/2009 | Suzuki et al. | |
| 7,577,232 B2* | 8/2009 | Tachibana et al. | 378/39 |
| 7,711,085 B2* | 5/2010 | Suzuki et al. | 378/39 |
| 2004/0258195 A1 | 12/2004 | Hara | |
| 2005/0063507 A1 | 3/2005 | Baba et al. | |
| 2006/0256921 A1* | 11/2006 | Tachibana et al. | 378/116 |
| 2007/0030950 A1 | 2/2007 | Sa et al. | |
| 2007/0030951 A1* | 2/2007 | Park et al. | 378/38 |
| 2007/0030952 A1* | 2/2007 | Sa et al. | 378/39 |
| 2007/0081624 A1 | 4/2007 | Nabatame | |
| 2009/0041191 A1 | 2/2009 | Suzuki et al. | |
| 2010/0172462 A1* | 7/2010 | Tancredi et al. | 378/4 |
| 2012/0039436 A1* | 2/2012 | Bothorel et al. | 378/11 |

FOREIGN PATENT DOCUMENTS

| | | |
|---|---|---|
| EP | 1 752 099 A | 2/2007 |
| JP | 09-122118 | 5/1997 |
| JP | 2007526103 | 9/2007 |
| JP | 2007526104 | 9/2007 |
| JP | 4280793 | 6/2009 |
| JP | 4313376 | 8/2009 |
| JP | 2010503510 | 2/2013 |
| WO | WO2004/075118 | 9/2004 |
| WO | WO2006/013325 | 2/2006 |
| WO | WO2006/109808 A1 | 10/2006 |
| WO | WO 2007/018332 | 2/2007 |
| WO | WO 2007/018333 | 2/2007 |
| WO | WO 2008/028988 | 3/2008 |
| WO | WO 2008/035953 | 3/2008 |
| WO | WO 2008/092009 | 7/2008 |
| WO | WO2010/128404 | 11/2010 |

OTHER PUBLICATIONS

PCT International Search Report completed on Aug. 11, 2010 for International Application No. PCT/IB2010/001298, 2 pages.

S.Y.Lee, et al., "Development of a Digital Panoramic X-ray Imaging System for Dental Applications," 2007 IEEE Nuclear Science Symposium Conference Record, vol. 4, pp. 2987-2990, 2007.

* cited by examiner

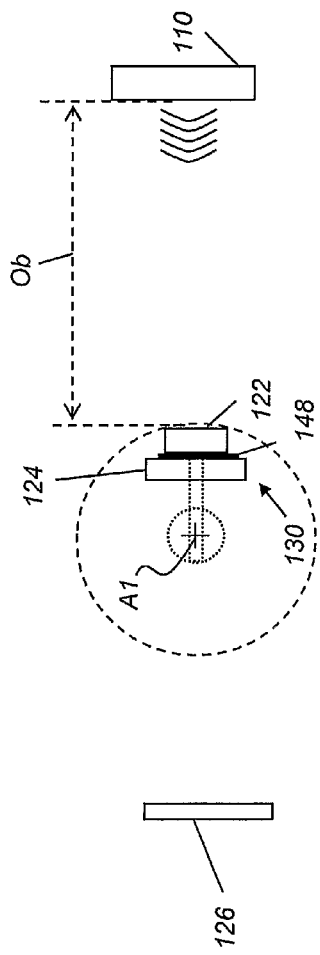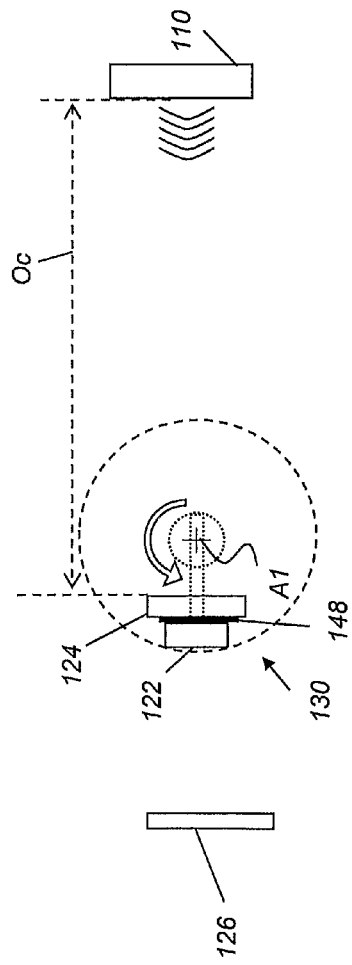

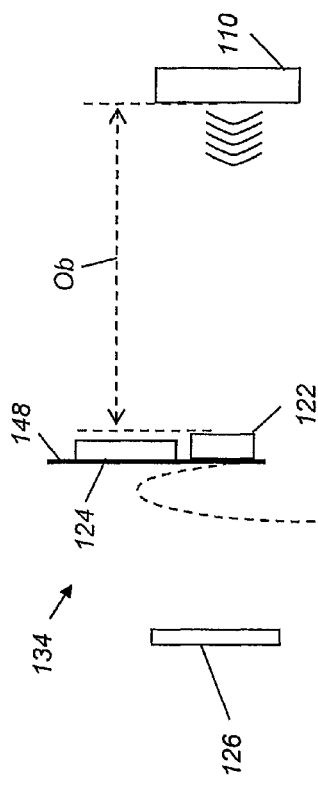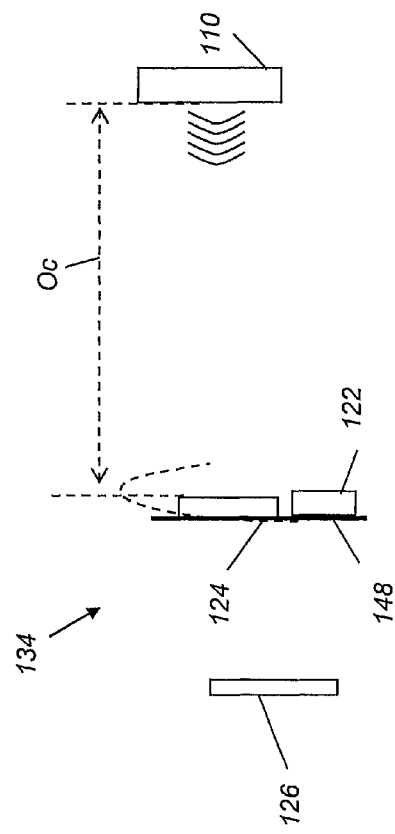

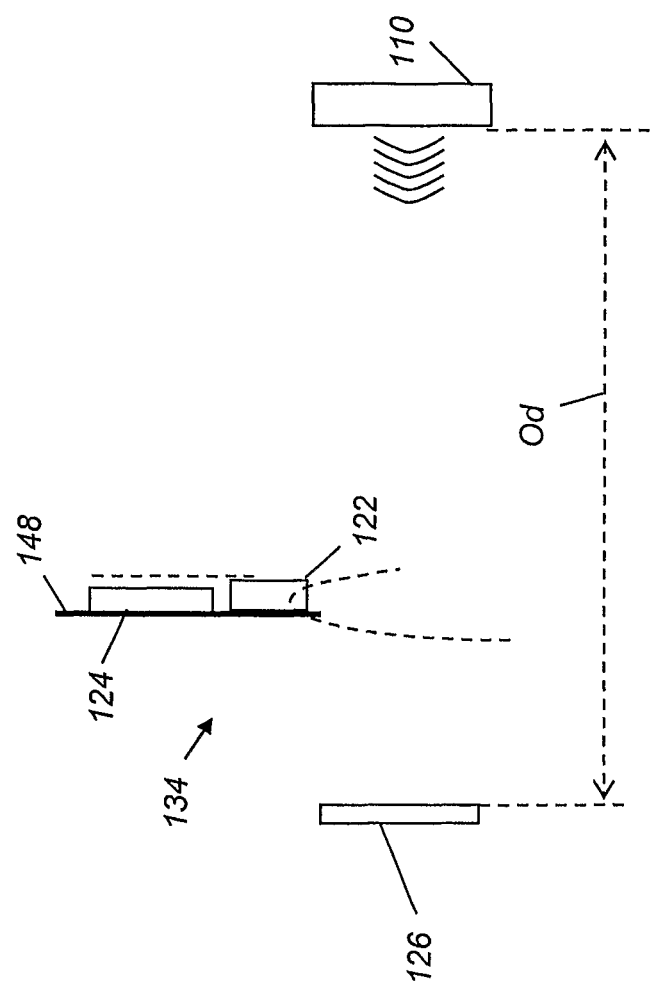

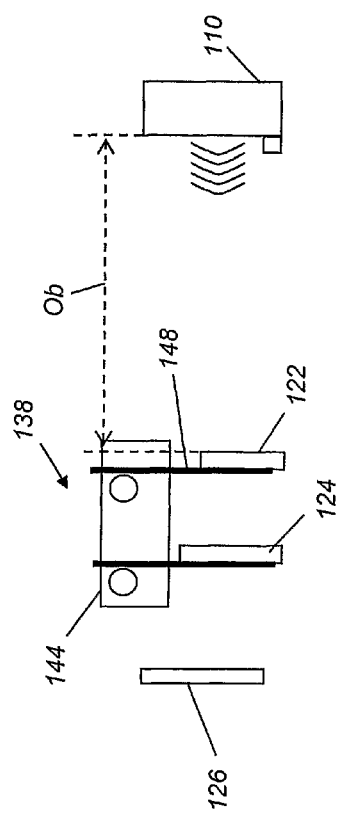
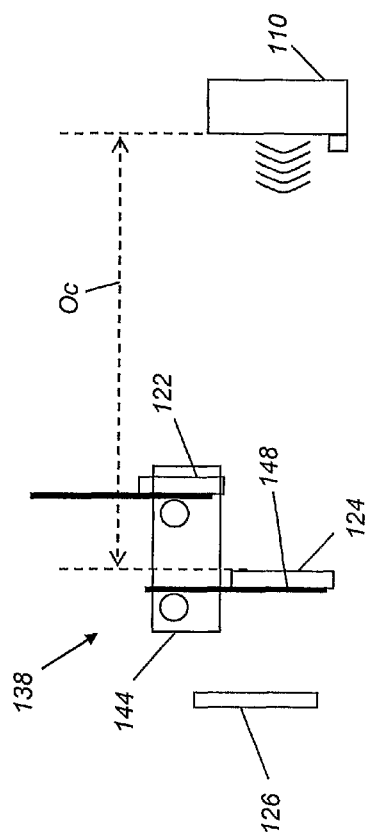

COMBINED PANORAMIC AND COMPUTED TOMOGRAPHY APPARATUS

CROSS REFERENCE TO RELATED APPLICATIONS

Priority is claimed from Provisional U.S. Ser. No. 61/175,095 filed on May 4, 2009, entitled "COMBINED PANORAMIC AND COMPUTED TOMOGRAPHY APPARATUS", in the name of Bothorel et al.

FIELD OF THE INVENTION

The invention relates generally to the field of imaging, and in particular to imaging in different x-ray modes for dental applications. More specifically, the invention relates to a combined panoramic and computed tomography apparatus.

BACKGROUND OF THE INVENTION

In conventional diagnostic imaging, different imaging systems are conventionally used in order to obtain images of different types, even where the same type of radiation source is used for two or more different types of images. Thus, for example, separate computed tomography (CT) and x-ray panoramic systems have been used for obtaining different types of images of the same patient using x-ray exposure.

Combination systems that provide both CT and panoramic x-ray imaging have been proposed. For example, U.S. Pat. No. 6,118,842 entitled "X-RAY IMAGING APPARATUS" to Arai et al. discloses an X-ray imaging apparatus for both CT imaging and panoramic imaging. The apparatus includes an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, only one large area X-ray detector is used. The X-ray imaging apparatus can obtain both types of images by switching modes during the imaging session. However, the proposed imaging apparatus performs both CT and panoramic imaging using only one detector. This requires an expensive detector capable of carrying out both imaging functions in a satisfactory manner. Additionally, in order to provide both image types, the proposed solution of Arai et al. compromises image quality by using a uniform distance between the X-ray source and detector, even though different distances would be more advantageous.

U.S. Pat. No. 7,236,563 entitled "COMBINED PANORAMIC AND COMPUTED TOMOGRAPHY PHOTOGRAPHING APPARATUS" to Sa et al. describes a combination system that allows both CT and panoramic imaging using two separate sensors or detectors. By way of example, FIG. 1 in the present application shows an embodiment of the Sa et al. '563 imaging system, a combined panoramic and CT imaging apparatus 400. The patient or other subject is positioned between an x-ray source part 410 and an x-ray sensor part 420. X-ray sensor part 420 rotates in order to position either a CT sensor 423 or a panoramic sensor 421 for obtaining the exposure. For CT imaging, CT sensor 423 is positioned behind the subject, relative to x-ray source part 410. The operator rotates CT sensor 423 into this position as part of imaging setup. Similarly, the operator rotates panoramic sensor 421 into position behind the subject as part of the setup for a panoramic imaging session.

Another system combines CT, panoramic, and cephalometric imaging from a single apparatus. U.S. Pat. No. 7,424,091 entitled "COMBINED PANORAMIC, CT (COMPUTED TOMOGRAPHY) AND CEPHALOMETRIC PHOTOGRAPHING APPARATUS" to Park et al. describes such a system, shown by way of example in FIG. 2. A combined panoramic, CT, and cephalometric imaging apparatus 300 has similar radiation source and sensor components to the earlier system of FIG. 1 and adds a separate cephalometric imaging part 310, mounted on a separate arm 315.

While both Sa et al. '563 and Park et al. '091 combine these imaging functions, there is room for improvement. One problem common to both systems relates to sensor positioning for each specific type of imaging that is needed. In order to use any of the types of imaging available, the specific sensor type for that imaging must be suitably positioned in the path of exposure radiation. At the same time, the unused sensor or sensors must be moved out of the way, so that they do not obstruct the path of radiation to the appropriate sensor. For example, with respect to the Sa et al. '563 disclosure, panoramic sensor 421 must be either removed or repositioned in order to allow CT imaging; similarly, CT sensor 423 must be removed or repositioned during panoramic imaging. For the three-function device described in the Park et al. '091 disclosure, in order to use the cephalometric imaging function, both panoramic and CT sensors 421 and 423 must be moved out of the way of the radiation path between X-ray source part 410 and cephalometric imaging part 310. In addition, manual attachment of the sensor for cephalometric imaging is required, and other manual repositioning of components appears to be needed in order to perform cephalometric imaging.

Thus, there is a need for a combined imaging apparatus that provides improved mechanisms for positioning detectors for panoramic, CT, and cephalometric imaging.

SUMMARY OF THE INVENTION

An object of the present invention is to advance the art of diagnostic imaging, particularly for dental applications. With this object in mind, the present invention provides a combined imaging apparatus for x-ray imaging of a subject in multiple modes, the apparatus comprising a supporting structure having an extended rotary arm, wherein the rotary arm comprises: (i) a computed tomography detector and a panoramic imaging detector, both mounted adjacently against a movable platen; and (ii) a detector positioning apparatus that is actuable to translate the position of the movable platen to either of at least first and second positions with respect to an x-ray source, wherein the first position disposes the computed tomography detector in the direct path of an x-ray source and wherein the second position disposes the panoramic imaging detector in the direct path of the x-ray source.

The combined computed tomography and panoramic imaging apparatus of the present invention provides different types of image detectors along a single rotary arm for positioning relative to the patient. This simplifies the operator's task of positioning components for imaging and is more favorable for automation of the setup process for each imaging type.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5B shows the use of the detector positioning apparatus of FIG. 5A for CT imaging.

FIG. 5C shows the use of the detector positioning apparatus of FIG. 5A for panoramic imaging.

FIG. 6B shows the use of the detector positioning apparatus of FIG. 6A for CT imaging.

FIG. 6C shows the use of the detector positioning apparatus of FIG. 6A for panoramic imaging.

FIG. 6D shows the use of the detector positioning apparatus of FIG. 6A for cephalometric imaging.

FIG. 7B shows the use of the detector positioning apparatus of FIG. 7A for CT imaging.

FIG. 7C shows the use of the detector positioning apparatus of FIG. 7A for panoramic imaging.

DETAILED DESCRIPTION OF THE INVENTION

Figure 1:
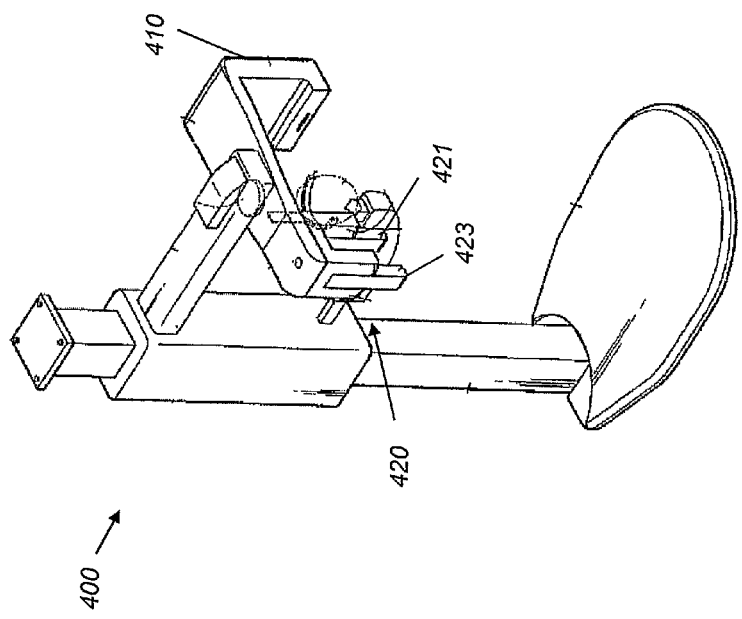
FIG. 1 shows a prior art imaging apparatus that provides both CT and panoramic x-ray imaging.
Figure 2:
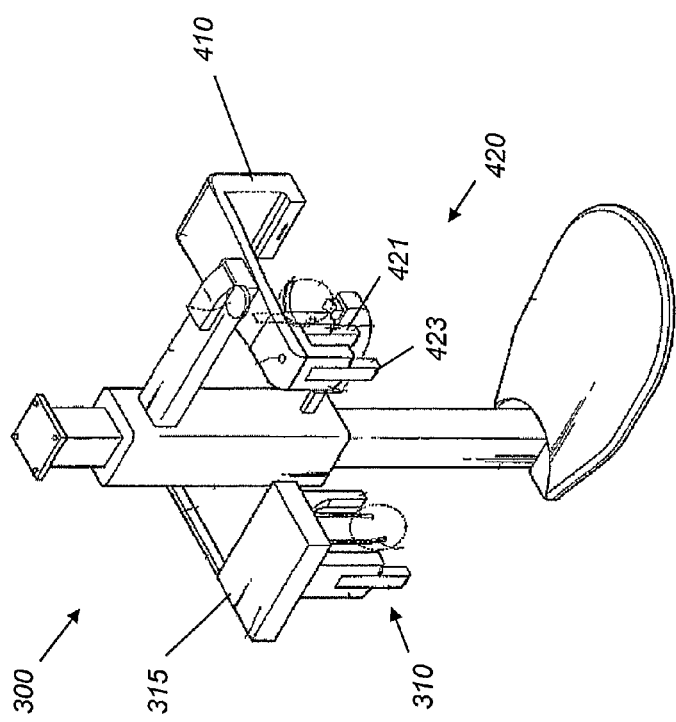
FIG. 2 shows a prior art imaging apparatus that provides both CT and panoramic x-ray imaging and adds cephalometric imaging capability.

The following is a detailed description of the preferred embodiments of the invention, reference being made to the drawings in which the same reference numerals identify the same elements of structure in each of the several figures.

Embodiments of the present invention address the need for a combined panoramic, CT (Computed Tomography) and cephalometric imaging apparatus. Referring to the perspective view of FIG. 3, a combined imaging apparatus 100 for panoramic, computed tomography and cephalometric imaging has a base 195, a support pole 190, and an elevation member 170 mounted on support pole 190. Elevation member 170 adjusts over a range of vertical positions to adapt for patient height. A rotary arm supporting member 150 extends from an upper portion of elevation member 170. A rotary arm 140 is supported by rotary arm supporting member 150 and provides, at one end, an x-ray source 110 that is energizable to provide exposure radiation along an exposure path and, at the other end, an x-ray detector apparatus 120. X-ray source 110 is in a fixed position relative to rotary arm 140 in one embodiment. In an alternate embodiment, x-ray source 110 can be separately mounted and moved toward or away from x-ray detector apparatus 120, in the x-direction as noted in FIG. 3. Not shown in FIG. 3, but required for an imaging apparatus of this type, is the needed support apparatus for providing power, data connection, and other functions.

The patient or other subject to be imaged is positioned between x-ray source 110 and x-ray detector apparatus 120, as shown in more detail subsequently. As is familiar to those skilled in the diagnostic imaging arts, a number of patient support devices, not specifically shown in FIG. 3 or described herein, may also be provided for helping to stabilize and position the head of the patient, including a chin supporting member, for example.

The description that follows is primarily concerned with devices and mechanisms for positioning the various detectors needed for combined panoramic, CT (Computed Tomography) and cephalometric imaging, as provided in embodiments of the present invention. Other aspects and features of combined imaging apparatus 100 structure and operation are known to those skilled in the art and described, for example, in previously cited Sa et al. '563 and Park et al. '091 disclosures, applicable parts of which are hereby incorporated by reference. This includes various motors, actuators, and other devices that help to support positioning of various system components.

Figure 4:
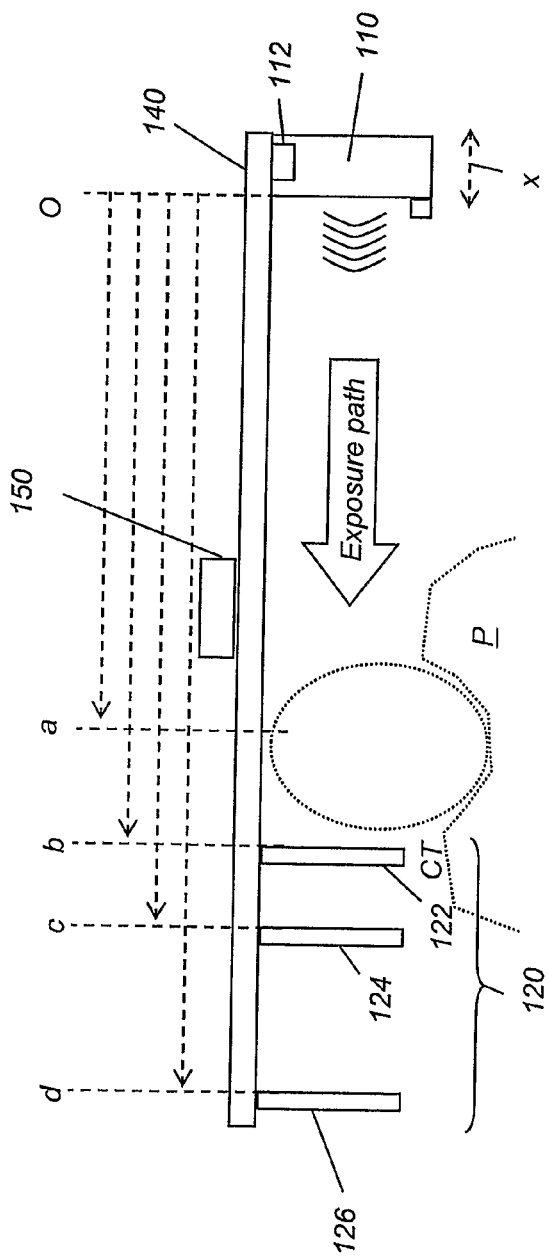
FIG. 4 shows a schematic view of source-to-detector distances that apply for each type of imaging that is performed by apparatus of the present invention.

FIG. 4 is a schematic view of source-to-detector distances along an exposure path from x-ray source 110, at a position labeled O, that apply for each type of imaging that is performed by apparatus of the present invention. Distance Oa refers to the distance to the subject/patient. Three detector components within rotary arm 140 are shown: a CT detector 122 at a distance Ob along the exposure path from x-ray source 110, a panoramic detector 124 at a distance Oc, and an optional cephalometric detector 126 at a distance Od. Distances Ob, Oc, and Od can vary for each different type of imaging that is performed, based on factors such as detector size, needed magnification ratio, relative position of the subject, collimation, and other factors related to x-ray imaging. The relative position of a subject, shown as patient P, in the exposure path with respect to x-ray source 110 and to the various detectors 122, 124, and 126 is represented in dotted outline. The exposure path extends horizontally, in the x-direction as shown in FIG. 4, along the rotary arm 140. Collimation at x-ray source 110 is used to substantially constrain exposure radiation to this linear path. An optional source translation apparatus 112 can be provided for moving x-ray source 110 in the proper direction along or orthogonal to the horizontal x-axis as shown. Shown subsequently are various arrangements of components that are used for positioning the desired detector 122, 124, or 126 in place for each type of imaging that is performed.

As noted earlier in the background section, various mounting techniques were described for properly positioning x-ray detectors for imaging, including a number of arrangements that required manual mounting or dismounting of detectors for each imaging mode. Embodiments of the present invention provide a number of improvements to these conventional techniques, particularly showing methods that allow automated adjustment to detector positions for each type of imaging.

Referring now to FIGS. 5A-5D and FIGS. 6A-6D, there is shown an arrangement for positioning, supporting, and moving the various CT, panoramic, and cephalometric detectors 122, 124, and 126 in one embodiment.

Figure 5A:
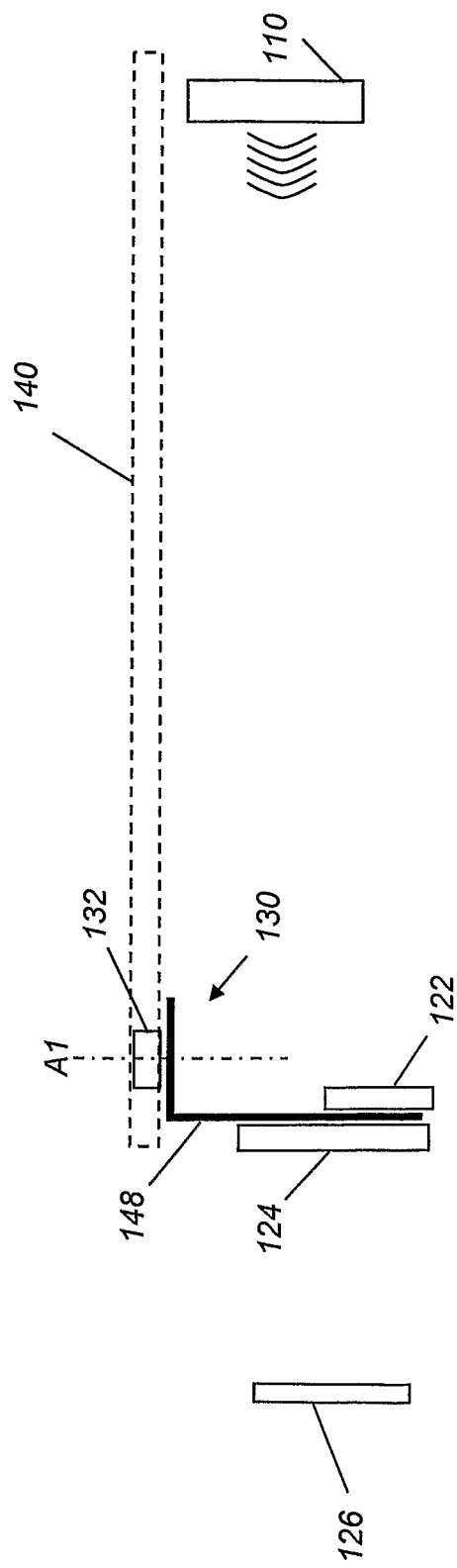
FIG. 5A shows an embodiment of a three-position detector positioning apparatus of the present invention.

FIG. 5A is a side view that shows a three-position detector positioning apparatus 130 with a movable platen 148 that is used to mount CT and panoramic detectors 122 and 124 adjacently, either back to back as shown in FIGS. 5A-5D, or side-by-side as shown in FIGS. 6A-6D. In the context of the present disclosure, a platen is considered to be a single protruding support element that extends in a direction that is orthogonal to the length of rotary arm 140. For reference, the relative position of rotary arm 140 is shown in dashed line form in FIGS. 5A and 6A. The platen itself could be in the form of a plate or other structure that provides one mounting surface or two mounting surfaces that are substantially in parallel. The platen is movable as a single element to provide rotational or other curvilinear translation of its corresponding detectors and could have variable thickness.

Figure 5D:
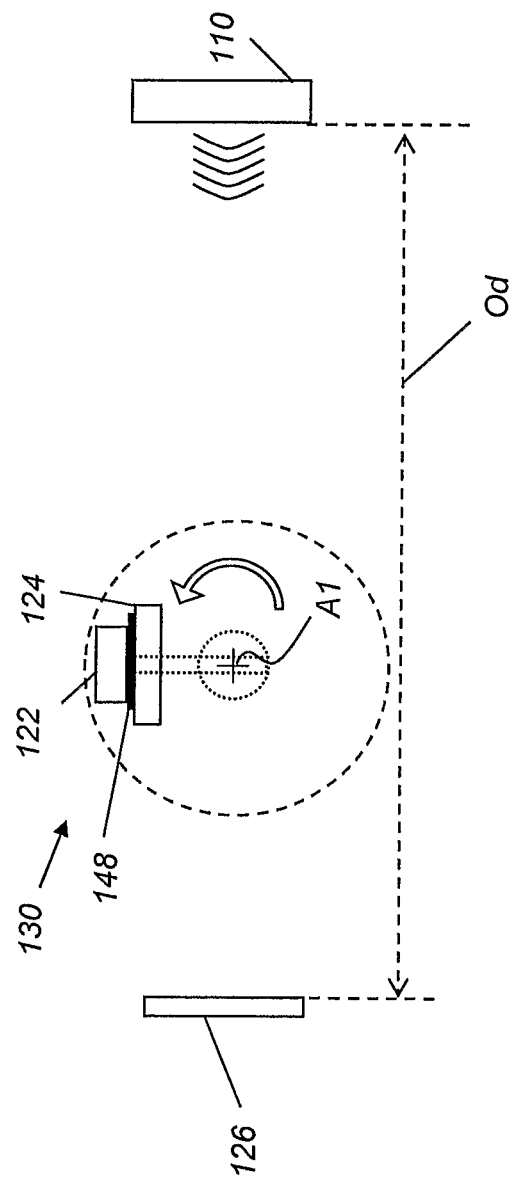
FIG. 5D shows the use of the detector positioning apparatus of FIG. 5A for cephalometric imaging.

CT and panoramic detectors 122 and 124 mount back-to-back on a movable platen 148 in the FIG. 5A embodiment. Movable platen 148, driven by a drive 132, rotates about a vertical rotation axis A1 to a suitable position for each of the two or three imaging types. Axis A1 is substantially orthogonal to the length of rotary arm 140, as shown in the FIG. 5A embodiment. FIGS. 5B, 5C, and 5D are each top views, taken along rotation axis A1 to show detector positioning for each of three detector types. FIG. 5B shows a top view with movable platen 148 of detector positioning apparatus 130 translated to a first position for CT imaging. In this configuration, CT detector 122 is properly positioned on the direct path of, unobstructed with respect to, and in line with, x-ray source 110 at distance Ob. FIG. 5C shows a top view with movable platen 148 of detector positioning apparatus 130 rotated to a second position for panoramic imaging. In this next configuration, panoramic detector 124 is positioned at distance Oc along the exposure path and is in the direct path of, unobstructed with respect to, and in line with x-ray source 110. FIG. 5D shows a top view with movable platen 148 of detector positioning apparatus 130 moved to a third position for cephalometric imaging, translated to displace detectors 122 and 124 so that they are out of the exposure path between x-ray source 110 and cephalometric detector 126. In this third position, cephalometric detector 126 is unobstructed with respect to, in the direct path of, and in line with x-ray source 110. In the FIG. 5A-5D embodiment, rotational translation of the movable platen between first and second positions is with respect to a vertical axis or, more generally, to an axis that is orthogonal to the length of rotary arm 140.

Figure 6A:
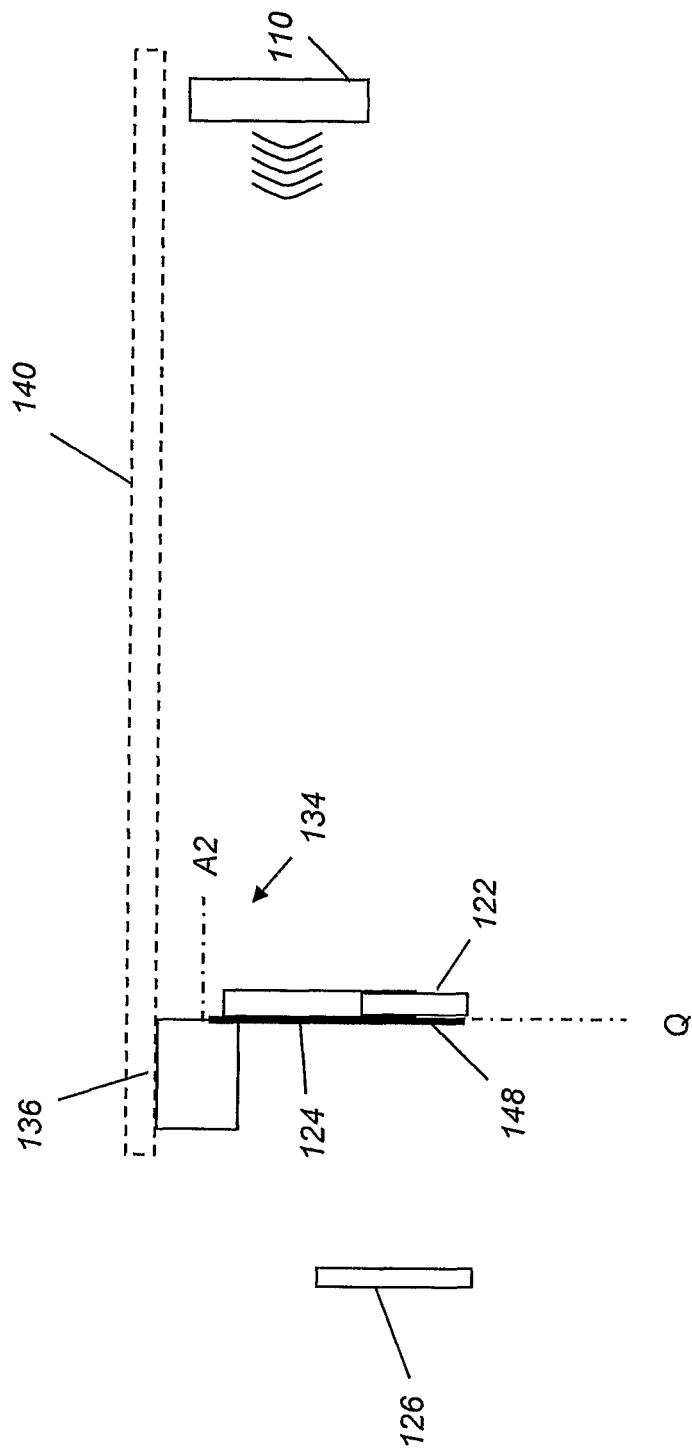
FIG. 6A shows an alternate embodiment of a three-position detector positioning apparatus.

Referring now to FIGS. 6A-6D, there is shown an alternate embodiment for positioning, supporting, and moving the various CT, panoramic, and cephalometric detectors 122, 124, and 126. In this embodiment, detectors 122 and 124 mount adjacently, such as side-by-side or top-to-bottom, on the same side of movable platen 148. Movable platen 148 translates detector position relative to the plane of the platen, shown for reference as Q in FIG. 6A. FIG. 6A is a side view that shows a three-position detector positioning apparatus 134 having an x-y translation drive 136 for detector positioning. Detector positioning apparatus 134 provides a curvilinear translation path for the detectors in a plane orthogonal to an axis A2 that is substantially parallel to the length of rotary arm 140. FIGS. 6B, 6C and 6D are each top views showing detector positioning for each of three detector types.

FIG. 6B shows a top view with movable platen 148 of detector positioning apparatus 134 translated to a first position for CT imaging. In this configuration, CT detector 122 is properly positioned at distance Ob along the exposure path, unobstructed with respect to, and in the direct path of x-ray source 110.

FIG. 6C shows a top view with movable platen 148 of detector positioning apparatus 134 translated to a second position for panoramic imaging. In this configuration, panoramic detector 124 is positioned at distance Oc along the exposure path, unobstructed with respect to, and in the direct path of x-ray source 110. Distances Ob and Oc can be the same in this embodiment.

FIG. 6D shows a top view with movable platen 148 of detector positioning apparatus 134 moved to a third position for cephalometric imaging, with movable platen 148 translated to remove detectors 122 and 124 out of the path between x-ray source 110 and cephalometric detector 126 so that cephalometric detector 126 is unobstructed with respect to, and in the direct path of x-ray source 110.

In the FIG. 6A-6D embodiment, curvilinear translation of the movable platen between first and second positions is in a plane that is orthogonal with respect to the length of rotary arm 140. Curvilinear translation within the plane can be provided by a rotary actuator or by one or more linear actuators, for example.

Figure 7A:
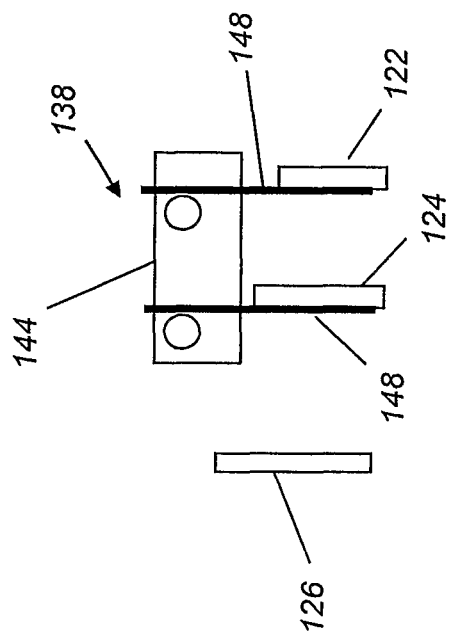
FIG. 7A shows another alternate embodiment of a three-position detector positioning apparatus.
Figure 7D:
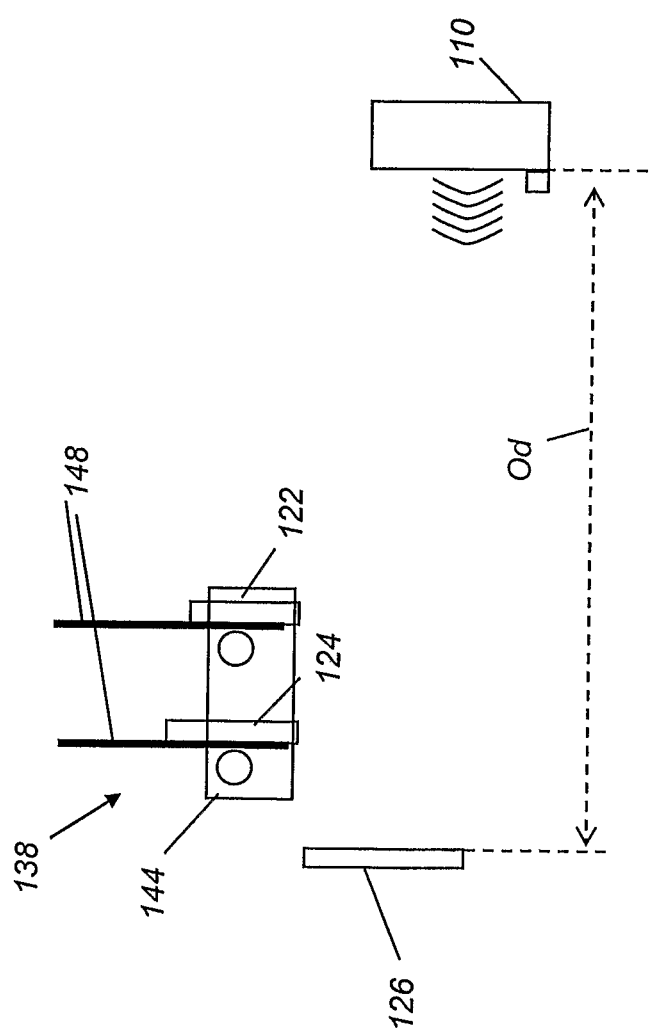
FIG. 7D shows the use of the detector positioning apparatus of FIG. 7A for cephalometric imaging.

Referring to FIGS. 7A-7D, there is shown another alternate embodiment for positioning, supporting, and moving the various CT, panoramic, and cephalometric detectors 122, 124, and 126. Here, each of detectors 122 and 124 are on separate movable platens 148. FIG. 7A is a side view that shows a two-position detector positioning apparatus 138 having an elevator apparatus 144 for detector positioning. Here, elevator apparatus 144 is actuable to translate one or more of the detectors into or out of the exposure path in a direction that is orthogonal to the rotary arm. FIGS. 7B, 7C and 7D are each side views showing detector positioning for each of three detector types. FIG. 7B shows a side view with detector positioning apparatus 138 supporting detectors in a first position for CT imaging. Here, CT detector 122 is properly positioned unobstructed with respect to, and in the direct path of x-ray source 110 along the exposure path at distance Ob. FIG. 7C shows a side view with elevator assembly 144 of detector positioning apparatus 138 actuated to lift CT detector 122 out of the exposure radiation path to allow panoramic imaging. Here, panoramic detector 124 is positioned along the exposure path at distance Oc, unobstructed with respect to, and in the direct path of x-ray source 110. FIG. 7D shows a side view with elevator assembly 144 of detector positioning apparatus 138 actuated to lift panoramic detector 124 up and out of the exposure radiation path to allow cephalometric imaging. Both detectors 122 and 124 are translated by elevator 144, out of the path of exposure radiation between x-ray source 110 and cephalometric detector 126, so that cephalometric detector 126 is unobstructed with respect to, and in the direct path of x-ray source 110 on the exposure path at distance Od.

Each of the embodiments shown in FIGS. 5A-7D allows a measure of automation for setting up the proper detector in each position and for determining when the detector is suitably positioned so that imaging can proceed. For example, operator commands entered at an operator console (not shown) can be used to set up a second imaging type after a first image is obtained. Optionally, operator controls on rotary arm 140 can allow the imaging configuration to be shifted from one imaging type to another. Manual positioning may also be used, or some combination of manual and automated actuation for achieving each configuration.

Figure 3:
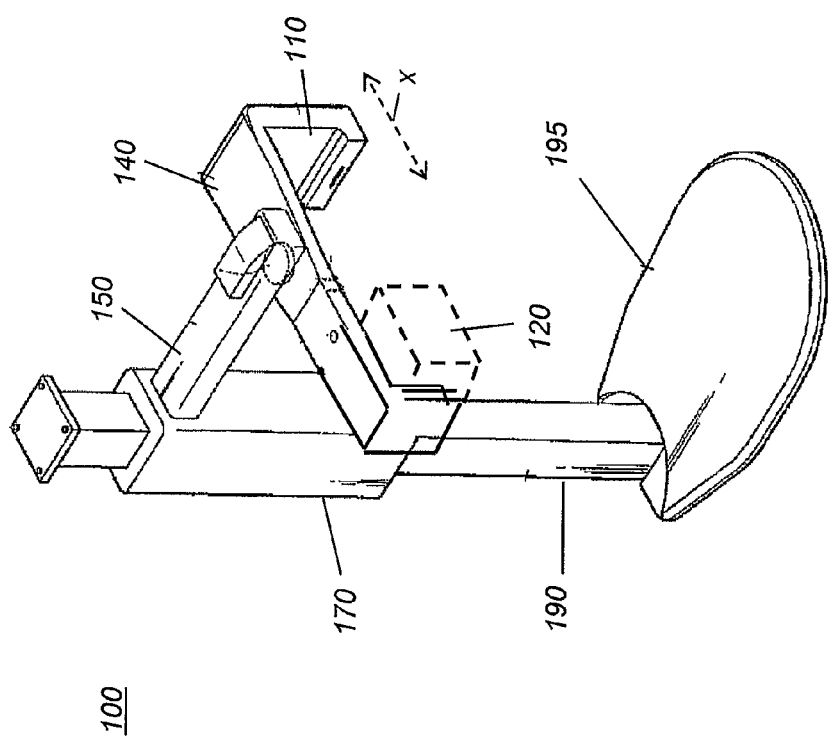
FIG. 3 shows an imaging apparatus according to an embodiment of the present invention.
Figure 8:
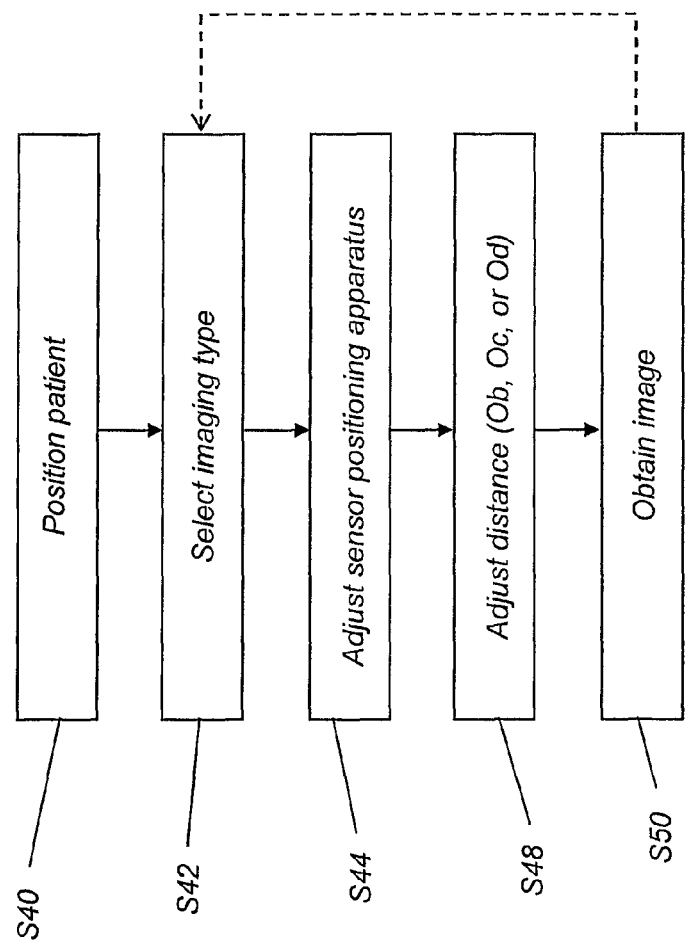
FIG. 8 shows a sequence of steps for acquiring one or more images using the apparatus of the present invention.

The sequence diagram of FIG. 8 summarizes the steps used for operator interaction when obtaining each type of image for combined imaging apparatus 100 in FIG. 3, using any of the detector positioning mechanisms described in FIGS. 5A-7D.

In a positioning step S40, the operator positions the patient for imaging, optionally using available chin rests or other support structures that are provided as part of rotary arm 140.

In an image selection step S42, the operator specifies the type of image to be obtained, whether CT, panoramic, or cephalometric. In one embodiment, this is specified by an operator instruction entered using any of a number of types of operator interface tools, for example, such as a keypad, touch-screen display, mouse or other pointer. Alternately, the operator may simply follow a manual sequence for equipment setup based on this selection.

A detector adjustment step S44 follows, in which the appropriate detector is positioned in the path of exposure radiation. Detector positioning can be performed manually, by operator manipulation of any of the mechanisms used for detector positioning apparatus, such as those shown in FIG. 5A, 6A, or 7A. Alternately, detector positioning can be at least partially automated, using the detector positioning apparatus to translate the various detectors into or out of the exposure radiation path so that the appropriate detector obtains the exposure energy.

An optional distance adjustment step S48 then adjusts the proper distance between x-ray source 110 and the receiving detector. This can be done using source translation apparatus 112 (FIG. 3) or using some other adjustment mechanism that is part of rotary arm 140.

An image acquisition step S50 follows, during which the subject is exposed and the selected image type is obtained. A looping operation, as indicated in dashed lines, then allows selection and acquisition of an alternate image type from the same subject. Looping can be executed automatically, such as where multiple image acquisitions are programmed for execution prior to imaging and further operator interaction is not required.

Detectors 122, 124, and 126 can be radiographic receivers of any type, including digital detectors that directly convert the exposure energy into digital data, computed radiography (CR) phosphor storage material that is removed from combined imaging apparatus 100 and scanned to obtain the acquired image, or sensitized x-ray film. Detectors can be area or line detectors.

Additional adjustment devices can be provided for changing the length of rotary arm 140 in order to achieve suitable distances Ob, Oc, and Od.

The invention has been described in detail with particular reference to a presently preferred embodiment, but it will be understood that variations and modifications can be effected within the spirit and scope of the invention. For example, the combined imaging apparatus could be wall- or ceiling-mounted, having some other suitable type of supporting structure rather than provided on a base as shown in the embodiment of FIG. 3. The relative spatial arrangements of the individual detectors could be changed from that shown in the examples, so that panoramic detector 124 is at less distance from the x-ray source than CT detector 122, (that is, so that distance Oc<distance Ob as in the sequence of FIG. 5A-5D or 6A-6D) for example. Detectors could be modular and removable, so that a single detector module could be used in either panoramic, CT, or cephalometric positions. The x-ray source could be mounted on the rotary arm or could be separately mounted. Detector positioning apparatus 130 (FIG. 5A-5D) or 134 (FIGS. 6A-6D) could alternately be moved along the direction of rotary arm 140 for providing the needed distance between x-ray source 110 and its corresponding detector.

The presently disclosed embodiments are therefore considered in all respects to be illustrative and not restrictive. The scope of the invention is indicated by the appended claims, and all changes that come within the meaning and range of equivalents thereof are intended to be embraced therein.

Parts List

100. Combined imaging apparatus
110. X-ray source
112. Source translation apparatus
120. x-ray detector apparatus
122. CT Detector
124. Panoramic detector
126. Cephalometric detector
130. Detector positioning apparatus
132. Rotation drive
134. Detector positioning apparatus
136. Translation drive
138. Detector positioning apparatus
140. Rotary arm
144. Elevator apparatus
148. Platen
150. Rotary arm supporting member
170. Elevation member
190. Support pole
195. Base
300. Combined panoramic, CT, and cephalometric imaging apparatus
310. Cephalometric imaging part
315. Arm
400. Combined panoramic and CT imaging apparatus
410. X-ray source part
420. X-ray detector part
421. Panoramic detector
423. CT detector
S40. Positioning step
S42. Image selection step
S44. Detector adjustment step
S48. Distance adjustment step
S50. Image acquisition step
Oa, Ob, Oc, Od. Distance
P. Patient
Q. Plane
x. Directional axis

What is claimed is:

1. A combined imaging apparatus for x-ray imaging of a subject in multiple modes, the imaging apparatus comprising a supporting structure having an extended rotary arm, wherein the rotary arm comprises:
   a computed tomography detector and a panoramic imaging detector, both mounted on the same side of a movable platen; and
   a detector positioning apparatus actuable to translate the position of the movable platen along a curvilinear path to either of at least first and second positions with respect to an x-ray source,
   wherein the first position disposes the computed tomography detector in the direct path of an x-ray source and wherein the second position disposes the panoramic imaging detector in the direct path of the x-ray source, wherein curvilinear translation of the movable platen is within a plane that is substantially orthogonal to an axis that is substantially parallel to the length of the extended rotary arm.

2. The combined imaging apparatus of claim 1 wherein the first position is a different distance from the x-ray source than the second position.

3. The combined imaging apparatus of claim 1 wherein curvilinear translation is provided by one or more linear actuators.

4. The combined imaging apparatus of claim 1 further comprising a cephalometric detector spaced apart from the movable platen and wherein the detector positioning apparatus is further actuable to translate the position of the movable platen to a third position that translates both the computed tomography detector and the panoramic imaging detector out of the direct path of the x-ray source.

5. The combined imaging apparatus of claim 4 wherein at least one of the computed tomography, panoramic, and cephalometric detectors is a computed radiography detector.

6. The combined imaging apparatus of claim 1 wherein at least one of the computed tomography and panoramic detectors is a digital detector.

7. The combined imaging apparatus of claim 1 wherein at least one of the computed tomography and panoramic detectors uses a sensitized film.

8. The combined imaging apparatus of claim 1 wherein one or more of the detectors is an area detector.

9. The combined imaging apparatus of claim 1 wherein a cephalometric detector is also mounted to the rotary arm.

10. A method for providing computed tomography, panoramic, and cephalometric imaging of a subject from the same imaging apparatus, comprising:
providing a supporting structure including an extended rotary arm having a detector positioning apparatus and an x-ray source both respectively mounted thereon;
configuring the detector positioning apparatus to one of three positions that dispose a selected detector that is either a computed tomography detector, or a panoramic detector, or a cephalometric detector in an unobstructed, in-line relationship to the x-ray source that is mounted on the extended rotary arm; and
energizing the x-ray source to obtain an image at the selected detector, wherein the computed tomography detector and the panoramic imaging detector are mounted on the same side of a movable platen, and wherein configuring the detector positioning apparatus comprises curvilinear translation of the movable platen within a plane that is substantially orthogonal to the length of the extended rotary arm.

11. The method of claim 10 wherein configuring the detector positioning apparatus comprises moving the movable platen to a third position that translates both the computed tomography detector and the panoramic imaging detector out of the direct path of the x-ray source.

12. A combined imaging apparatus for computed tomography, panoramic, and cephalometric imaging of a subject, the apparatus comprising:
an x-ray source; and
a supporting structure having an extended rotary arm;
a cephalometric detector mounted at a first distance Od from the x-ray source; and
a detector positioning apparatus mounted to the rotary arm and adjustable to a first configuration, a second configuration, and a third configuration, where the detector positioning apparatus includes a movable platen that rotates about an axis orthogonal to the rotary arm, where a computed radiography detector and a panoramic detector are provided on different sides of the movable platen, and rotation of the detector positioning apparatus alone provides the first configuration, the second configuration, and the third configuration;
wherein the first configuration disposes the computed tomography detector at an unobstructed position in line with the x-ray source at a second distance Ob along the exposure path;
wherein the second configuration disposes the panoramic detector at an unobstructed position in line with the x-ray source at a third distance Oc along the exposure path; and
wherein the third configuration displaces both the computed tomography detector and the panoramic detector away from the exposure path to dispose the cephalometric detector at an unobstructed position in line with the x-ray source along the exposure path.

13. The apparatus of claim 12 wherein at least one of the computed tomography and panoramic detectors is a digital detector, where rotation of the movable platen alone provides the first configuration, the second configuration, and the third configuration.

14. The apparatus of claim 12 wherein at least one of the computed tomography and panoramic detectors uses a sensitized film.

15. The apparatus of claim 12 wherein at least one of the computed tomography, panoramic, and cephalometric detectors is a computed radiography detector.

16. The combined imaging apparatus of claim 12 wherein the computed tomography detector and the panoramic imaging detector are mounted along opposite sides of the movable platen and translation of the movable platen between first and second positions is rotation of the movable platen with respect to an axis that is substantially orthogonal to the length of the extended rotary arm.

17. A method for providing computed tomography, panoramic, and cephalometric imaging of a subject from the same imaging apparatus, comprising:
providing a supporting structure including an extended rotary arm having a detector positioning apparatus mounted thereto;
configuring the detector positioning apparatus to one of three positions that dispose a selected detector that is either a computed tomography detector, a panoramic detector, or a cephalometric detector in an unobstructed, inline relationship to the x-ray source that is mounted on the extended rotary arm;
rotating only the detector positioning apparatus to provide the first configuration, the second configuration, and the third configuration; and
energizing the x-ray source to obtain an image at the selected detector,
where the detector positioning apparatus includes a movable platen that rotates about an axis orthogonal to the rotary arm, where the computed radiography detector and the panoramic detector are provided at opposite sides of the movable platen;
wherein the first configuration disposes the computed tomography detector at an unobstructed position in line with the x-ray source at a second distance Ob along the exposure path;
wherein the second configuration disposes the panoramic detector at an unobstructed position in line with the x-ray source at a third distance Oc along the exposure path; and
wherein the third configuration displaces both the computed tomography detector and the panoramic detector away from the exposure path to dispose the cephalometric detector at an unobstructed position in line with the x-ray source along the exposure path.

* * * * *